United States Patent [19]
Owens et al.

[11] Patent Number: 5,610,183
[45] Date of Patent: Mar. 11, 1997

[54] PHENYLGLYCINE DERIVATIVES PHARMACEUTICAL COMPOSITIONS CONTAINING THEM AND THEIR USE IN THERAPY

[75] Inventors: Andrew P. Owens, Rushden; Brian J. Williams, Great Dunmow, both of United Kingdom

[73] Assignee: Merck, Sharp & Dohme Ltd., Hoddesdon, United Kingdom

[21] Appl. No.: 167,870

[22] PCT Filed: Jul. 8, 1992

[86] PCT No.: PCT/GB92/01241

§ 371 Date: Dec. 17, 1993

§ 102(e) Date: Dec. 17, 1993

[87] PCT Pub. No.: WO93/01165

PCT Pub. Date: Jan. 21, 1993

[30] Foreign Application Priority Data

Jul. 10, 1991 [GB] United Kingdom ............... 9114886
Apr. 2, 1992 [GB] United Kingdom ............... 9207278

[51] Int. Cl.⁶ .................. A61K 31/195; C07C 255/03; C07C 271/10; C07C 233/00
[52] U.S. Cl. .................. 514/539; 514/567; 514/617; 514/620; 514/650; 514/651; 514/653; 558/388; 558/406; 560/27; 560/29; 560/30; 562/433; 562/452; 564/164; 564/165; 564/167; 564/308; 564/309; 564/310; 564/317; 564/346
[58] Field of Search .................. 514/539, 567, 514/617, 620, 650, 651, 653; 560/27, 29, 30; 562/433, 452; 564/164, 165, 167, 308, 309, 310, 311, 317, 346; 558/406, 388

[56] References Cited

U.S. PATENT DOCUMENTS 4,044,047 8/1977 Gleason ............... 544/54
5,245,080 9/1993 Aubard et al. ............... 564/346

FOREIGN PATENT DOCUMENTS 0194464   9/1986  European Pat. Off. .
0297782A1 1/1989  European Pat. Off. .
0330940   9/1989  European Pat. Off. .
0394989A3 10/1990 European Pat. Off. .
0522808   1/1993  European Pat. Off. .
2396737   2/1979  France .

2054588A  2/1991  United Kingdom .

OTHER PUBLICATIONS

The Journal of Antibiotics, vol. XXXV No. 3, pp. 329–334, 1982.
J. Pharm. Pharmacol, 42, 546–552, 1990.
Dolence et al. J. Med. Chem. 1991, 34, pp. 956–968.
CA102: 113120, 1985.
CA83:10111, 1975.
J. Am. Chem. Soc., 1985, 107, 1698–1701.
J. of Med. Chem., vol. 34, No. 3, Mar. 1991, pp. 956–968, by E. K. Dolence, et al.
J. Chem. Soc., Perkin Trans, 1, 1985, pp. 1039–1044, by A. Bewick, et al.
J. Am. Chem. Soc., 1985, 107, pp. 1698–1701, by L. E. Overman, et al.
Chem. Abstracts, vol. 100, May 21, 1984, No. 21.

Primary Examiner—Yogendra N. Gupta
Attorney, Agent, or Firm—Robert J. North; Melvin Winokur

[57] ABSTRACT

Compounds of Formula (I) and pharmaceutically acceptable salts thereof:

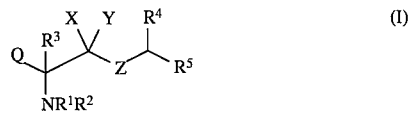

wherein

Q is optionally substituted phenyl or naphthyl;

X and Y are each H, $C_{1-6}$alkyl, $C_{2-6}$alkenyl or X and Y are together =O;

Z is O or S;

$R^1$ is H, optionally substituted $C_{1-6}$alkyl, optionally substituted phenyl ($C_{1-4}$alkyl), $C_{2-6}$alkenyl, $COC_{1-6}$alkylhalo, $COR^a$, $COOR^a$, $CONHR^a$, $COC_{1-6}$alkyl$NR^aR^b$ or $CONR^aC_{1-6}$alkyl$CONR^aR^b$;

$R^2$ is substituted $C_{1-6}$alkyl, optionally substituted phenyl($C_{1-4}$alkyl), $C_{2-6}$alkenyl, $C_{1-6}$alkylhalo, $COR^a$, $COOR^a$, $CONHR^a$, $COC_{1-6}$alkyl$NR^aR^b$ or $CONR^aC_{1-6}$alkyl$CONR^aR^b$;

or $R^1$ and $R^2$ together form a chain $(CH_2)_p$ optionally substituted by oxo;

$R^3$ is H [or $C_{1-6}$alkyl];

$R^4$ is H, $C_{1-6}$alkyl or phenyl; and $R^5$ is optionally substituted $(CH_2)_q$phenyl; are tachykinin antagonists useful for treating pain.

11 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Arg Pro Lys Pro Gln Gln Phe Phe Gly Leu Met
    1                   5                   10

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

His Lys Thr Asp Ser Phe Val Gly Leu Met
    1                   5                   10

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (i v) ANTI-SENSE: NO (x i) SEQUENCE DESCRIPTION: SEQ ID NO:3:

Asp Met His Asp Phe Phe Val Gly Leu Met
1               5                   1 0

PHENYLGLYCINE DERIVATIVES PHARMACEUTICAL COMPOSITIONS CONTAINING THEM AND THEIR USE IN THERAPY

This application is A 371 of PCT/GB92/01241.

This invention relates to a class of aromatic compounds, which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg-Pro-Lys-Pro-Gln-Gln-Phe-Phe-Gly-Leu-Met-$NH_2$
Neurokinin A:
His-Lys-Thr-Asp-Ser-Phe-Val-Gly-Leu-Met-$NH_2$
Neurokinin B:
Asp-Met-His-Asp-Phe-Phe-Val-Gly-Leu-Met-$NH_2$ Substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (December 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al, Science (1990) 250, 279–82], in senile dementia of the Alzheimer type, Alzheimer's disease and Down's Syndrome. Substance P may also play a role in demyelinating diseases such as multiple sclerosis and amyotrophic lateral sclerosis [J. Luber-Narod et. al., poster to be presented at C.I.N.P. XVIIIth Congress, 28th Jun.-2nd Jul., 1992, in press], and in disorders of bladder function such as bladder detrusor hyperreflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), ophthalmic disease such as conjuctivitis, vernal conjunctivitis, and the like, and cutaneous diseases such as contact dermatitis, atropic dermatitis, urticaria, and other eczematoid dermatitis (European patent application no. 0 394 989).

In view of their metabolic instability, peptide derivatives are likely to be of limited utility as therapeutic agents. It is for this reason that non-peptide tachykinin receptor antagonists are sought.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

European patent application no. 0 194 464 discloses compounds of formula (A):

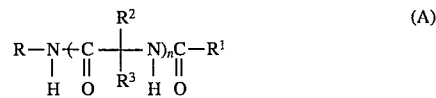

wherein:

$R^1$ is loweralkyl, arylloweralkyl or optionally substituted phenyl;

$R^2$ is inter alia phenyl;

$R^3$ is inter alia H or loweralkyl;

R is inter alia arylloweralkyl; and n is inter alia 1.

The compounds are said to have anticonvulsant properties.

German patent application no. 28 51 435 discloses compounds of formula (B):

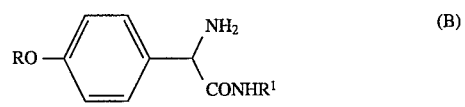

wherein:

R is H or $CH_3$; and $R^1$ is inter alia a loweralkyl group substituted by an optionally substituted phenyl group.

The compounds are said to be useful in heart disease, obesity and diabetes, through their effect on carbohydrate metabolism.

Canadian patent application no 2,029,338 discloses compounds of formula (C):

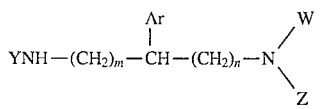

wherein

Ar is optionally substituted phenyl, 1- or 2-naphthyl or 5- or 6-membered heteroaryl;
m is inter alia zero;
Y is H,

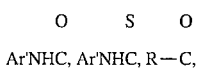

RCH$_2$ or

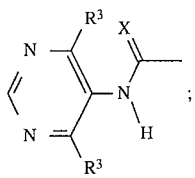

n is inter alia 1;
W is inter alia H or C$_{1-20}$alkyl; and
Z is inter alia R—CH$_2$, where R is inter alia optionally substituted phenyl.

The compounds are said to be ACAT inhibitors useful in lowering blood cholesterol levels.

Dutch patent application no. 8003601 discloses compounds of formula (D):

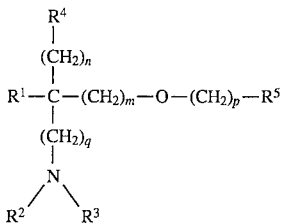

wherein
R$^1$ is C$_{1-10}$ alkyl;
R$^2$ and R$^3$ are H or C$_{1-10}$alkyl;
R$^4$ is inter alia optionally substituted phenyl;
R$^5$ is inter alia optionally substituted phenyl;
n is inter alia zero;
m is inter alia 1;
p is inter alia 1; and
q is inter alia zero.

The compounds are said to have anti-spasmolytic, anaesthetic and analgesic activity.

European patent applicaiton no. 0 384 088 discloses (+) 2-N,N-dimethylamino-1-(3,4,5-trimethoxyphenyl)methyloxy)-2-phenylbutane as an opiate receptor ligand of use in the treatment of gastrointestinal disorders.

The present invention provides a compound of formula (I), or a salt or prodrug thereof:

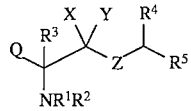

wherein
Q represents optionally substituted phenyl, optionally substituted heteroaryl or optionally substituted naphthyl;
X and Y each represent H, C$_{1-6}$alkyl, C$_{2-6}$alkenyl or X and Y together form a group =O;
Z represents O or S;
R$^1$ represents H; C$_{1-6}$ alkyl optionally substituted by hydroxy, cyano, COR$^a$, COOR$^a$, CONR$^a$R$^b$, COC$_{1-4}$alkylNR$^a$R$^b$, CONR$^a$C$_{1-4}$alkylCONR$^a$R$^b$ or NR$^a$R$^b$, (where R$^a$ and R$^b$ each independently represent H, C$_{1-6}$ alkyl, phenyl optionally substituted by one or more of C$_{1-6}$alkyl, C$_{1-6}$alkoxy, halo or trifluoromethyl or phenyl(C$_{1-4}$alkyl) optionally substituted in the phenyl ring by one or more of C$_{1-6}$ alkyl, C$_{1-6}$ alkoxy, halo or trifluoromethyl); phenyl(C$_{1-4}$ alkyl), (optionally substituted in the phenyl ring by one or more of C$_{1-6}$ alkyl, C$_{1-6}$ alkoxy, halo or trifluoromethyl); C$_{2-6}$ alkylene; COR$^a$; COOR$^a$; CONHR$^a$; COC$_{1-6}$alkylhalo; COC$_{1-6}$alkylNR$^a$R$^b$; or CONR$^a$C$_{1-6}$alkylCONR$^a$R$^b$, where R$^a$ and R$^b$ are as previously defined;

R$^2$ represents C$_{1-6}$ alkyl substituted by hydroxy, cyano, COR$^a$, COOR$^a$, CONR$^a$R$^b$, COC$_{1-4}$alkylNR$^a$R$^b$, CONR$^a$C$_{1-4}$alkylCONR$^a$R$^b$ or NR$^a$R$^b$, (where R$^a$ and R$^b$ are as above defined); phenyl(C$_{1-4}$ alkyl), (optionally substituted by one or more of C$_{1-6}$ alkyl, C$_{1-6}$ alkoxy, halo and trifluoromethyl in the phenyl ring); C$_{2-6}$ alkylene; COR$^a$; COOR$^a$; CONHR$^a$; COC$_{1-6}$alkylhalo; COC$_{1-6}$alkylNR$^a$R$^b$; or CONR$^a$C$_{1-6}$alkylCONR$^a$R$^b$, where R$^a$ and R$^b$ are as previously defined;

or R$^1$ and R$^2$ together form a chain (CH$_2$)$_p$ optionally substituted by oxo; where p is 4 or 5 and where one methylene group may optionally be replaced by an oxygen atom or a group NR$^x$, where R$^x$ is H or C$_{1-6}$ alkyl;

R$^3$ represents H or C$_{1-6}$alkyl;

R$^4$ represents H, C$_{1-6}$ alkyl or phenyl (optionally substituted by one or more of C$_{1-6}$ alkyl, C$_{2-6}$ alkenyl, C$_{2-6}$ alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, where R$^c$ and R$^d$ each independently represent H, C$_{1-6}$ alkyl, phenyl or trifluoromethyl); and R$^5$ represents (CH$_2$)$_q$phenyl, wherein q is 0, 1, 2 or 3, which may optionally be substituted in the phenyl ring by one or more of C$_{1-6}$ alkyl, C$_{2-6}$ alkenyl, C$_{2-6}$ alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, where R$^c$ and R$^d$ are as above defined; with the exception of N-(tert-butyoxycarbonyl)-D-4-hydroxyphenylglycine benzyl ester, 1-acetamido-2-benzylthio-1-phenylethane, 1-((cyanomethyl)amino)-2-benzyloxy-1-phenylethane and α-(acetyl-methylamino)-α-methyl-5-fluoro-2,4-dioxo-3,4-dihydro-1(2H)-pyrimidineacetic acid, phenylmethylester.

The alkyl, alkenyl and alkynyl groups referred to with respect to any of the above formulae may represent straight, branched or cyclic groups or a combination thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Where Q represents optionally substituted phenyl, heteroaryl or naphthyl, suitable substituents include C$_{1-6}$ alkyl, C$_{2-6}$ alkenyl, C$_{2-6}$ alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, (where R$^c$ and R$^d$ are as above defined), such as C$_{1-6}$ alkyl, C$_{2-6}$ alkenyl, C$_{2-6}$ alkynyl, halo, cyano, nitro, trifluoromethyl, SCH$_3$, SOCH$_3$, SO$_2$CH$_3$, OR$^b$, NR$^b$R$^c$, NR$^b$COR$^c$, NR$^b$COOR$^c$, COOR$^b$ or CONR$^b$R$^c$, where R$^b$ and R$^c$ are as above defined. One or more substituents may be present and each may be located at any available ring position.

Suitable values of the group Q include phenyl, indolyl, naphthyl, thiophenyl, furanyl, pyridyl, indazolyl, imidazolyl, tetrazolyl, oxazolyl, benzothiophenyl, benzofuranyl and benzimidazolyl.

Preferably Q is optionally substituted phenyl, indolyl, furanyl, thiophenyl or naphthyl. More preferably Q represents optionally substituted phenyl.

Preferably X and Y each represents H.

Preferably Z represents O.

In one subgroup of compounds according to the invention, R$^1$ represents H; C$_{1-6}$ alkyl optionally substituted by hydroxy, cyano, COR$^a$, COOR$^a$, CONR$^a$R$^b$, COC$_{1-4}$alkylNR$^a$R$^b$, CONR$^a$C$_{1-4}$alkylCONR$^a$R$^b$ or NR$^a$R$^b$, (where R$^a$ and R$^b$ each are as previously defined); phenyl(C$_{1-4}$ alkyl) (optionally substituted by one or more of C$_{1-6}$ alkyl, C$_{1-6}$ alkoxy, halo and trifluoromethyl in the phenyl ring); C$_{2-6}$ alkylene; COR$^a$; COOR$^a$; CONHR$^a$; COC$_{1-4}$alkylNR$^a$R$^b$; or CONR$^a$C$_{1-4}$alkylCONR$^a$R$^b$ (where R$^a$ and R$^b$ are as previously defined) and R$^2$ represents C$_{1-6}$alkyl substituted by hydroxy, cyano, COR$^a$, COOR$^a$, CONR$^a$R$^b$, COC$_{1-4}$alkylNR$^a$R$^b$, CONR$^a$C$_{1-4}$alkylCONR$^a$R$^b$ or NR$^a$R$^b$, (where R$^a$ and R$^b$ each as previously defined); phenyl(C$_{1-4}$ alkyl) (optionally substituted by one or more of C$_{1-6}$ alkyl, C$_{1-6}$ alkoxy, halo and trifluoromethyl in the phenyl ring); C$_{2-6}$ alkylene; COR$^a$; COOR$^a$; CONHR$^a$; COC$_{1-4}$alkylNR$^a$R$^b$; or CONR$^a$C$_{1-4}$alkylCONR$^a$R$^b$ (where R$^a$ and R$^b$ are as previously defined), or R$^1$ and R$^2$ together form a chain (CH$_2$)$_p$ optionally substituted by oxo where p is 4 or 5 and where one methylene group may optionally be replaced by an oxygen atom or a group NR$^x$, where R$^x$ is H or C$_{1-6}$ alkyl.

In a further subgroup of compounds according to the invention R$^1$ represents H, C$_{1-6}$alkyl, phenyl(C$_{1-4}$alkyl), COR$^{16}$, COOR$^{16}$ or CONHR$^{16}$, where R$^{16}$ is C$_{1-6}$alkyl or phenyl, and R$^2$ represents phenyl(C$_{1-4}$alkyl), COR$^{16}$, COOR$^{16}$ or CONHR$^{16}$, where R$^{16}$ is as previously defined Suitable values for the group R$^2$ include C$_{1-6}$alkyl substituted by, for example, cyano, hydroxy, NH$_2$, CO$_2$C$_{1-6}$alkyl, COR$^a$, CONR$^a$R$^b$, CONR$^a$CH$_2$CONR$^a$R$^b$, especially CONHCH$_2$CONH$_2$, CON(CH$_3$)CH$_2$CONH(CH$_3$) or CON(CH$_3$)CH$_2$CON(CH$_3$)$_2$, COC$_{1-4}$alkylNR$^a$R$^b$, especially COCH$_2$NR$^a$R$^b$, such as COCH$_2$NH$_2$, C$_{1-6}$ alkenyl, especially allyl and formyl, and chains such as (CH$_2$)$_4$, (CH$_2$)$_5$ and (CH$_2$)$_2$O(CH$_2$)$_2$.

Suitable values for R$^1$ include those mentioned above for R$^2$, and especially H and C$_{1-6}$alkyl, such as methyl, ethyl, propyl and cyclopropylmethyl.

In a preferred group of compounds according to the invention, R$^1$ represents H or methyl and R$^2$ represents C$_{1-2}$alkyl substituted by a group selected from hydroxy, cyano, CHO, CO$_2$(C$_{1-6}$alkyl), CONR$^a$R$^b$ and NR$^a$R$^b$. More preferably R$^1$ represents H and R$^2$ represents CH$_2$CONH$_2$.

Suitable values for the group R$^3$ include H and methyl, preferably H.

Preferably R$^4$ represents H.

Suitably R$^5$ represents (CH$_2$)$_q$phenyl where q is 0, 1 or 2 and the phenyl group is substituted. Suitable phenyl substituents include methyl, methoxy, nitro, cyano, halo and trifluoromethyl. Preferably R$^5$ represents a substituted phenyl group. More preferably R$^5$ represents 3,5-dimethylphenyl or 3,5-bistrifluoromethylphenyl.

A preferred sub-group of compounds according to the invention is represented by formula (Ia)

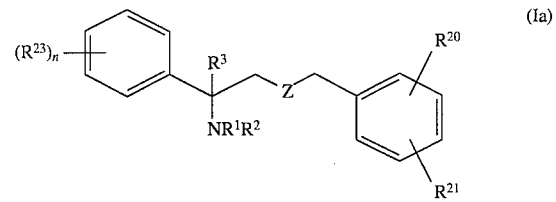

(Ia)

wherein

R$^1$, R$^2$, R$^3$ and Z are as defined for formula (I) above;

R$^{20}$ and R$^{21}$ each independently represent H, C$_{1-6}$ alkyl, C$_{2-6}$ alkenyl, C$_{2-6}$ alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, where R$^c$ and R$^d$ are as above defined;

each R$^{23}$ represents C$_{1-6}$ alkyl, C$_{2-6}$ alkenyl, C$_{2-6}$ alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, where R$^c$ and R$^d$ are as above defined, preferably halo, such as chloro;

n is 0, 1, 2 or 3, preferably 0;

and salts and prodrugs thereof.

Particularly preferred are compounds of formula (Ia) wherein R$^{20}$ and R$^{21}$ are other than H and are located in the 3- and 5-positions. Preferably R$^{20}$ and R$^{21}$ each represent methyl or, more preferably, trifluoromethyl.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when both R$^1$ and R$^2$ are other than hydrogen, the nitrogen atom to which they are attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, including diabetic and chemotherapy-induced neuropathy, and postherpetic and other neuralgias; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. For example, the compounds of formula (I) may suitably be used in the treatment of disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I), or N-(tert-butyoxycarbonyl)-D-4-hydroxyphenylglycine benzyl ester, 1-acetamido-2-benzylthio-1-phenylethane, 1-((cyanomethyl)amino)-2-benzyloxy-1-phenylethane or α-(acetyl-methylamino)-α-methyl-5-fluoro-2,4-dioxo-3,4-dihydro-1(2H)-pyrimidineacetic acid, phenylmethylester, for use in therapy.

In the treatment of conditions involving actions of tachykinins released physiologically in response to noxious or other stimuli, a suitable dosage level is about 0.001 to 50 mg/kg per day, preferably about 0.005 to 10 mg/kg per day, and especially about 0.005 to 5 mg/kg per day. The compounds may be administered on a regimen of 1 to 4 times per day, preferably once daily.

According to a further or alternative aspect, the present invention provides a method of treatment of a human or animal subject suffering from or susceptible to a condition characterised by the presence of an excess of tachykinin which method comprises administering to a human or animal subject in need of such treatment an effective amount of a compound of formula (I), or N-(tert-butyoxycarbonyl)-D-4-hydroxyphenylglycine benzyl ester, 1-acetamido-2-benzylthio-1-phenylethane, 1-((cyanomethyl)amino)-2-benzyloxy-1-phenylethane or α-(acetyl-methylamino)-α-methyl-5-fluoro-2,4-dioxo-3,4-dihydro-1(2H)-pyrimidineacetic acid, phenylmethylester or a salt or prodrug thereof.

The present invention also provides the use of a compound of formula (I), or N-(tert-butyoxycarbonyl)-D-4-hydroxyphenylglycine benzyl ester, 1-acetamido-2-benzylthio-1-phenylethane, 1-((cyanomethyl)amino)-2-benzyloxy-1-phenylethane or α-(acetyl-methylamino)-α-methyl-5-fluoro-2,4-dioxo-3,4-dihydro-1(2H)-pyrimidineacetic acid, phenylmethylester, or a salt or prodrug thereof, for the manufacture of a medicament for the treatment of conditions characterised by the presence of an excess of tachykinins.

According to one general process (a) the compounds according to the invention may be prepared by reaction of a compound of formula (II)

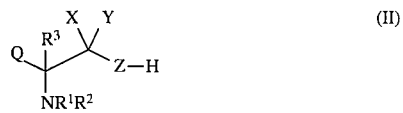

wherein Q, $R^1$, $R^2$, $R^3$, X, Y and Z are defined as for formula (I), with a compound of formula $HalCHR^4R^5$, where $R^4$ and $R^5$ are as defined for formula (I) and Hal is halo, such as bromo, chloro or iodo, in the presence of a base.

The reaction is conveniently carried out in a suitable organic solvent, such as ether, for example, tetrahydrofuran.

Suitable bases of use in the reaction include alkali or alkaline earth metal hydrides, for example, sodium hydride.

According to an alternative process, (b), compounds of formula (I) wherein $R^1$ and $R^3$ are H may be prepared from intermediates of formula (IIIA)

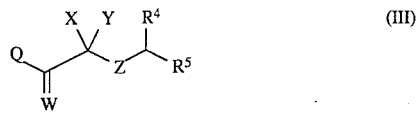

wherein Q, X, Y, Z, $R^4$ and $R^5$ are as defined for formula (I) and W represents NOH (IIIA) via a process which comprises reduction.

Suitable reducing agents of use in the reduction include borane, catalytic hydrogenation in the presence of a suitable catalyst, such as a nobel metal catalyst, for example palladium, which may be supported, for example, on carbon, nickel, dissolving metal reduction, for example using an alkali metal, such as sodium, in an alcohol, such as ethanol, or sodium amalgam.

A preferred reducing agent is borane. The borane reduction is preferably effected at elevated temperature, such as about 105°–110° C.

Compounds of formula (I) may also be prepared from other compounds of formula (I). Thus, for example, compounds of formula (I) wherein $R^1$ represents H may be reacted with an optionally substituted alkylating or an acylating agent to produce compounds of formula (I) wherein $R^1$ represent an optionally substituted alkyl or an acyl group. Suitable procedures will be readily apparent to one skilled in the art.

Conversely, compounds of formula (I) wherein $R^1$ represents, for example, an acyl or a benzyl group, may be converted to compounds of formula (I) wherein $R^1$ represents H by, for example, hydrolysis or catalytic hydrogenation. Suitable reagents and conditions are described in the accompanying examples, or will be readily apparent to one skilled in the art of organic chemistry.

Compounds of formula (II) wherein Z is O and X and Y together represent a group =O are commercially available or may be prepared, for example, from intermediates of formula (IV)

wherein Q and $R^3$ are as above defined and Ph represents phenyl, by hydrolysis.

The reaction is conveniently effected by heating a solution of the compound of formula (IV) in concentrated hydrochloric acid at reflux.

Compounds of formula (II) wherein Z is O and X and Y are =O may also be prepared by conventional procedures for the preparation of amino acids which are well documented and are described, for example, in *Chemistry and Biochemistry of the Amino Acids,* ed. G. C. Barrett, Chapman and Hall, 1985.

Compounds of formula (II) wherein Z is S may be prepared from the corresponding compounds of formula (II) wherein Z is O by treating the latter compound with Lawesson's reagent or phosphorus pentasulphide in a suitable solvent, e.g. pyridine, at ambient or elevated temperature, suitably at the reflux temperature of the chosen solvent.

Compounds of formula (II) wherein X and Y represent H may be prepared from the corresponding compounds of formula (II) wherein X and Y together represent =O, by reduction.

Suitable reducing agents include metal hydrides, such as lithium aluminium hydride. The reaction is conveniently effected in a suitable organic solvent, such as ether, for example, tetrahydrofuran, suitably at elevated temperature, such as the reflux temperature of the solvent.

Intermediates of formula (IV) may be prepared from compounds of formula (V)

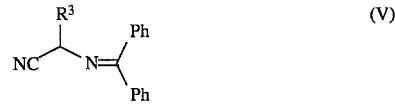

wherein $R^3$ is as defined for formula (I), by reaction with a compound of formula Q—Hal wherein Hal is halo, such as bromo, chloro or iodo, in the presence of a base.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethyl ammonium chloride.

Compounds of formula (V) are commercially available or may be prepared by procedures readily apparent to one skilled in the art.

Compounds of formula Q—Hal are commercially available or may be prepared by conventional procedures known to those skilled in the art.

Compounds of formula (IIIA) may be prepared from the corresponding compounds of formula (III) wherein W represents O (IIIB) by reaction with hydroxylamine or a suitable derivative thereof.

Conveniently the reaction will carried out in an aqueous organic solvent such as, for example, aqueous methanol. Preferably the reaction mixture will be buffered to approximately pH 4 by addition of a suitable salt, such as, for example sodium citrate.

Compounds of formula (IIIB) may be prepared by reaction of a compound of formula (VI)

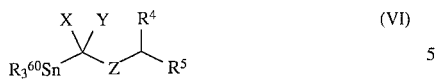

wherein X, Y, Z, $R^4$ and $R^5$ are as defined for formula (I) and $R^{60}$ represents an alkyl group, with a compound of formula Q—COHal, where Hal represents halo such as chloro or bromo and Q is as above defined, by the method described by J. W. Labadie et. al., *J. Org. Chem. Soc.*, 1983, 48, 4634.

Intermediates of formula (VI) may be prepared by analogous methods to that described by W. C. Still, *J. Am. Chem. Soc.*, 1978, 100, 1481.

Intermediates of formula (III) are novel compounds and form a further aspect of the present invention.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples 1, 2, 3, 4, 5, 10 and 11 illustrate the preparation of compounds according to the invention.

DESCRIPTION 1

1-(3,5-Dimethylphenyl)methyloxy)-(2S)-2-ammonium-2-phenylethane oxylate salt a) L-2-Phenylglycinol (5 g) and di-t-butyldicarbonate (9.4 g) was stirred in a dichloromethane solution (30 ml) at room temperature for 3 hours. The precipitate which formed was filtered to give N-t-butoxycarbonyl-L-2-phenylglycinol, 4 g.

b) N-t-Butoxycarbonyl-L-2-phenylglycinol (2 g, part (a), was dissolved in a mixture of dimethylformamide (2 ml) and tetrahydrofuran (10 ml). Sodium hydride (80%) was added to this over a 10 minute period with stirring under nitrogen at room temperature. After a further 15 min, 3,5-dimethylbenzyl bromide was added and the reaction left to stir for 4 hours. To the solution was added water (102 ml), and the product extracted into ethyl acetate. The organic phase was washed twice with water and dried ($MgSO_4$). The solvent was removed in vacuo and the residue chromatographed in a column containing silica gel eluting with 100% petrol (bp 60°–70° C.) and 5% ethyl acetate/95% petrol (bp 60°–80° C.), to give 1-(3,5-dimethylphenyl)methyloxy-(2S)-2-t-butoxycarbonylamino-2-phenylethane, 0.9 g, mp 46°–49° C. $^1$H NMR (360MHz, $CDCl_3$) δ 7.38–7.22 (5H, m), 6.90 (1H, s), 6.83 (2H, s), 5.28 (1H, bs), 4.84 (1H, bs), 4.46 (1H, d, Jgem=11.9Hz, $OCH_AH_BPh$), 4.38 (1H, d, Jgem=11.9Hz, $OCH_AH_BPh$), 3.69 (1H, dd, J=9.74Hz and 4.39Hz), 3.60 (1H, m), 2.28 (6H, s), 1.40 (9H, s). m/z ($CI^+$) 356 (M+H). Found: C, 74.37; H, 8.03; N, 3.97. $C_{22}H_{29}NO_3$ requires C, 74.33; H, 8.22; N, 3.94%.

c) 1-(3,5-Dimethylphenyl)methyloxy (2S)-2-t-butoxycarbonylamino-2-phenylethane (0.2 g; part (b)) was dissolved in trifluoroacetic acid for 10 mins then evaporated to dryness. To a solution of the residue dissolved in methanol was added oxalic acid (70 mg). The solvent was removed in vacuo and the residue recrystallized from diethylether/petrol (bp 60°–80° C.) to give the 1-(3,5-dimethylphenyl)methyloxy-(2S)-2-ammonium-2-phenylethane oxalate salt, 0.114 g, 135°–137° C. $^1$H NMR (360MHz, DMSO) δ 7.51–7.38 (5H, m), 6.90 (3H, s), 4.52 (1H, dd, J=7.37Hz and 5.0Hz), 4.48 (2H, d, J=1.8Hz), 3.76–3.66 (2H, m), 2.24 (6H, s). Found: C, 65.07; H, 6.61; N, 4.00. $C_{17}H_{21}NO.1.1C_2H_2O_4$ requires C, 65.07; H, 6.60; N, 3.95%.

EXAMPLE 1

L-1-((3,5-Bis(trifluoromethyl)phenyl)methyloxy)-2-(t-butoxycarbonylamino)-2-phenylethane 2-N-t-Butoxycarbonylamino-L-2-phenylglycinol (Description 1a, 1g) was alkylated with 3,5-bis(trifluoromethyl)benzyl bromide in a manner analogous to that described in Description 1b to give the title compound, mp 52°–53° C., m/e ($CI^+$)=464 (M+H), ($CI^-$)=462 (M−H). Found: C, 56.99; H, 4.67; N, 3.05: $C_{22}H_{22}F_6NO_3$ requires: C, 57.02; H, 5.00; N, 3.02%.

DESCRIPTION 2

L-2-Ammonium-1-((3,5-bis(trifluoromethyl)phenyl)methyloxy)-2-phenylethane oxalate salt L-1-((3,5-Bis(trifluoromethyl)phenyl)methyloxy)-2-t-butoxycarbonylamino-L-2-phenylglycinol (Example 1) was deprotected in an analogous manner to that described in Description 1c to give the title compound, mp 84°–90° C. $^1$H NMR (MeOH $d_4$, 360MHz) δ 7.97 (2H, s), 7.89 (1H, s), 7.47–7.41 (5H, m), 4.8 (2H, AB Jgem=12.7Hz), 4.61 (1H, t, J=5.93Hz), 3.9 (2H, d, J=5.27Hz). m/e ($CI^+$)=364. Found: C, 48.46; H, 3.75; N, 2.94. $C_{17}H_{15}F_6NO.1.4(C_2H_2O_4)$ requires C, 48.60; H, 3.67; N, 2.86%.

EXAMPLE 2

1-((3,5-Dimethylphenyl)methyloxy)-(2S)-2-(((Carbomethoxy)methyl)amino)-2-phenylethane 1-((3,5-Dimethylphenyl)methyloxy)-(2S)-2-t-butoxycarbonylamino-2-phenylethane (1.9 g, Description 1b) was treated with trifluoroacetic acid. After 10 minutes the solvent was removed in vacuo and the residue partitioned between dichloromethane and 2M-NaOH. The organic phase was washed with water, dried ($MgSO_4$) and evaporated in vacuo. To a solution of the residue in tetrahydrofuran (20 ml) was added methyl bromoacetate (0.51 ml) and triethylamine (0.56 g) and the solution heated to reflux for 16 hours. Ethyl acetate and water were added and the organic phase washed with water, saturated brine and dried ($MgSO_4$). The residue obtained after removal of the solvent in vacuo was chromatographed on silica gel eluting with ethyl acetate/petroleum ether bp 60°–80° C. (1:1) to give the title compound 1.6 g as an oil. Found: C, 73.13; H, 7.75; N, 4.32. $C_{20}H_{25}NO_3$ requires C, 73.37; H, 7.70; N, 4.28%.

EXAMPLE 3

(2S)-2-(((Carboxamido)methyl)ammonium)-1-((3,5-dimethylphenyl)methyloxy)-2-phenylethane oxalate salt The product of Example 2 (0.8 g) was dissolved in methanol (20 ml) saturated with ammonia at 0° C. After the solution had been stored at +5° C. for 4 days in a sealed flask the solution was evaporated to dryness and chromatographed on silica gel eluting with ethyl acetate. A solution of the product and oxalic acid in methanol was evaporated to dryness and the residue crystallised from hot diethyl ether to give the title compound, mp=86°–89° C. Found: C, 60.10; H, 6.35; N, 6.64. $C_{19}H_{24}N_2O_2.(C_2H_2O_4)_{1.3}$ requires C, 60.41; H, 6.24; N, 6.52%.

EXAMPLE 4

(2S)-1-((3,5-Bis(trifluoromethyl)phenyl)methyloxy)-2-(((carbomethoxy)methyl)ammonium)-2-phenylethane oxalate salt The title compound was prepared from (2S)-2-amino-2-phenyl-1-((bis(trifluoromethyl)phenyl)methyloxy)-2-phenylethane (Description 2) using an analogous procedure to that described in Example 2, mp 95°–97° C. Found: C, 49.33; H, 3.82; N, 2.61. $C_{20}H_{19}F_6NO_3.(C_2H_2O_4)_{1.2}$ requires C, 49.51; H, 3.97; N, 2.58%.

EXAMPLE 5

(2S)-1-((3,5-Bis(trifluoromethyl)phenyl)methyloxy)-2-(((carboxamido)methyl)ammonium)-2-phenylethane oxalate salt The title compound was prepared from the product of Example 4 using an analogous procedure to that described in Example 3, mp: 147°–151° C. Found: C, 49.35; H, 4.07; N, 5.47. $C_{19}H_{18}F_6N_2O_2.C_2H_2O_4$ requires C, 49.42; H, 3.95; N, 5.49%.

EXAMPLE 6

2-Ammonium-1-((3,5-bis(trifluoromethyl)phenyl)methyloxy)-2-(4-chlorophenyl)ethane oxalate salt monohydrate a) Potassium hydroxide (27.0 g), lithium chloride (6.75 g) and triethylbenzylammonium chloride (1.84 g) were dissolved in dichloromethane (40 ml) and 33% aqueous ammonia solution (45 ml) and gaseous ammonia bubbled through this solution at 0° C. for 5 minutes. A solution of p-chlorobenzaldehyde (11.2 g) and chloroform (10.2 ml) in dichloromethane (40 ml) was added over 1 hour whilst maintaining the temperature at 0° C. and this mixture stirred under a continuous stream of ammonia at 0° C. for 6 hours and at room temperature for a further 18 hours. Water (120 ml) and dichloromethane (40 ml) were added, the aqueous layer was further extracted with dichloromethane, concentrated in vacuo, filtered and adjusted to pH 6–7 with concentrated hydrochloric acid. On cooling to 0° C. a precipitate formed and was collected by filtration, washed with ethanol and water and dried to give α-(4-chlorophenyl)glycine, 4.2 g.

b) The amino acid (part (a), 4.2 g) was added portionwise to a refluxing suspension of lithium aluminium hydride (1.2 g) in tetrahydrofuran (72 ml) and the mixture heated under reflux for a further 6 hours. The solution was cooled to room temperature and 10% sodium hydroxide solution (1.92 ml) added dropwise followed by water (2.4 ml). A solution of di-tert-butyl dicarbonate (7.0 g) and 4-dimethylaminopyridine (96 mg) in dichloromethane (38 ml) was added and the resulting mixture heated under reflux for 6 hours then cooled to room temperature and filtered through a pad of anhydrous sodium sulphate. The resulting crude mixture was purified by chromatography on silica gel to give 2-(N-t-butoxycarbonylamino)-2-(4-chlorophenyl)ethanol.

c) The product (part (b), 1.0 g) was alkylated with 3,5-bis(trifluoromethyl)benzyl bromide followed by deprotection with trifluoroacetic acid in an analogous manner to that described in Example 2b and 2c respectively to give the title compound. Found: C, 45.19; H, 3.27; N, 2.61. $C_{17}H_{14}ClF_6NO. C_2H_2O_4.H_2O$ requires C, 45.12; H, 3.59; N, 2.78%.

EXAMPLE 7

2-Ammonium-1-((3,5-bis(trifluoromethyl)phenyl)methyloxy)-2-(3-chlorophenyl)ethane oxalate salt The title compound was prepared by a method analogous to that described in Example 6 using m-chlorobenzaldehyde as starting material. Found: C, 46.60; H, 3.37; N, 2.89. $C_{17}H_{14}ClF_6NO. C_2H_2O_4$ requires: C, 46.28; H, 3.31; N, 2.87%.

EXAMPLE 8

2-Ammonium-1-((3,5-bis(trifluoromethyl)phenyl)methyloxy)-2-(2-chlorophenyl)ethane oxalate salt a) Sodium hydride (80% suspension in oil, 2.03 g) was washed twice with petroleum ether and to this solid was added tetrahydrofuran (50 ml) and dimethylformamide (3 ml) followed by the slow addition of a solution of 3,5-bis(trifluoromethyl)benzyl alcohol (15 g) in tetrahydrofuran (50 ml). After the effervescence had subsided (30 minutes) a solution of tri-n-butyltinmethylene iodide (25.2 g) was added. The solution was heated to reflux for 2 hours, cooled to room temperature and quenched by careful addition of petroleum ether bp 60°–80° C. (500 ml) and water (200 ml). The organic phase was washed with water and dried ($MgSO_4$). After removal of the solvent in vacuo the residue was distilled under reduced pressure bp $_{0.8}$=140° C. to give tri-n-butyl-((3,5-bis(trifluoromethyl)phenyl) methyloxymethyl)tin. $^1H$ NMR (360MHz, $CDCl_3$) δ 7.78 (1H, s, aryl 4C$\underline{H}$), 7.76 (2H, s, aryl 2,6-C$\underline{H}$), 4.52 (2H, s, aryl-C$\underline{H}_2$).

b) 2-Chlorobenzoyl chloride (1.27 ml), tri-n-butyl-((3,5-bis(trifluoromethyl)phenyl)methyloxymethyl)tin (part (a), 6.2 g) and benzylchlorobis(triphenylphosphine)palladium (II) (80 mg) were dissolved in chloroform (10 ml) and the solution heated to 70° C. for 36 hours. On cooling diethyl ether and saturated aqueous potassium fluoride were added and this solution filtered through a pad of Hyflo. The organic layer was washed with water, dried ($MgSO_4$) and reduced in vacuo giving a residue which was purified by chromatography on silica gel to give 2'-chloro-2-((3,5-bis(trifluoromethyl)phenyl) methyloxy)acetophenone, $^1H$ NMR (360MHz, CDCl$_3$) δ 7.79 (3H, bs, bis(CF$_3$) aryl C H2,4,6), 7.54–7.26 (4H, m, aryl), 4.75 (2H, s), 4.76 (2H, s).

c) The product of part (b) (1.05 g), sodium acetate (1.06 g) and hydroxylmine hydrochloride were dissolved in methanol (20 ml) and the solution stirred for 24 hours. Water was added and the mixture extracted with diethyl ether. The organic layer was washed with water, dried (MgSO$_4$) and reduced in vacuo to give 2'-chloro-2-((3,5-bis(trifluoromethyl) phenyl)methyloxy)acetophenone oxime.

d) A solution of borane (10 ml, 1M in tetrahydrofuran) was added to a solution of the product of part (c) in tetrahydrofuran and the mixture heated under reflux for 48 hours. 5N hydrochloric acid was added and refluxing continued for 2 hours. On cooling diethyl ether was added and the solution washed with 2N aqueous sodium hydroxide. The organic layer was dried (MgSO$_4$) and reduced in vacuo to give a residue which was dissolved in methanol and treated with hydrogen gas at 50 psi over a 10% palladium on carbon catalyst for 2 hours. This mixture was filtered, reduced in vacuo and the residue partitioned between 5N hydrochloric acid and diethyl ether. The ether phase was washed with aqueous potassium hydroxide and dried (MgSO$_4$). Oxalic acid (150 mg) was added and the solution allowed to stand for 24 hours when the title compound was collected as a precipitate (200 mg). Found: C, 46.81; H, 3.63; N, 2.64%; C$_{17}$H$_{14}$ClF$_6$NO(COOH)$_2$ requires: C, 46.28; H, 3.31; N, 2.87%.

EXAMPLE 9

1-Ammonium-2-((bis(trifluoromethyl)phenyl)methyloxy)-1-phenylpropane oxalate salt hemihydrate a) To a cooled (–30° C.) solution of N-t-butoxycarbonyl (α-phenyl)glycine (40 g) and triethylamine (110 ml) in dimethyformamide (500 ml) was added iso-butylchloroformate (34.4 ml) at such a rate that the temperature of the solution remained below –20° C. After stirring for 15 minutes to the solution was added N,O-dimethylhydroxylamine hydrochloride (52 g) and CH$_2$Cl$_2$ (800 ml). The solution was stirred at room temperature for 16 hours. Ethyl acetate was added and the solution was washed with 10% aqueous citric acid solution, water (3 times), saturated NaHCO$_3$ solution and dried (MgSO$_4$). The solvent was removed in vacuo and the resultant solid washed with hexane to give N'-t-butoxycarbonyl (α-phenyl)glycine N,O-dimethylhydroxamate, 37 g.

b) To a cooled (0° C.) solution of the product of part (a) (1.0 g) in tetrahydrofuran (10 ml) was slowly added methyl magnesium bromide (6.8 ml). After stirring the solution at room temperature for 2 hours 10% aqueous citric acid and ethyl acetate were added and the organic phase washed further with water (2 times) and dried (MgSO$_4$). The solvent was removed in vacuo and to a solution of the residue in ethanol was added sodium borohydride (0.13 g) for 2 hours. The solvent was removed in vacuo and a solution of the residue in CH$_2$Cl$_2$ was washed with water (3 times) and dried (MgSO$_4$) to give upon evaporation in vacuo 1-N-t-butoxycarbonylamino-1-phenylpropan-2-ol as a mixture of diastereomers.

c) The product of part (b) was alkylated with 3,5-bis(trifluoromethyl)benzyl bromide in a manner analogous to that described in Description 1b to give 2-((bis(trifluoromethyl)phenyl)methyloxy)-1-(N-t-butoxycarbonylamino)-1-phenylpropane as a mixture (approx 3:1) of diastereomers. This material (0.56 g) was dissolved in trifluoroacetic acid (20 ml) for 10 minutes followed by evaporation in vacuo. A solution of the residue in CH$_2$Cl$_2$ was washed with 2N-NaOH, water (2 times), saturated brine and dried (MgSO$_4$). After removal of the solvent in vacuo the residue was crystallized by addition of oxalic acid (0.84 g) followed by recrystallization from diethyl ether/petroleum ether to give the title compound, mp 60°–62° C. Found: C, 50.17; H, 4.20; N, 2.84. C$_{18}$H$_{17}$F$_6$NO. C$_2$H$_2$O$_4$.0.5(H$_2$O) requires: C, 50.43; H, 4.23; N, 2.94%.

EXAMPLE 10

L-1-((3,5-Bis(trifluoromethyl)phenyl)methyloxy)-2-((Cyanomethyl)amino)-2-phenylethane A solution of L-2-Amino-1-(3,5-bis(trifluoromethyl)phenyl)methyloxy-2-phenylethane (1.5 g, Description 2, free base), bromoacetonitrile (0.5 g) and triethylamine (0.4 g) in tetrahydrofuran (10 ml) was heated under reflux for 6 hours. After cooling to room temperature and evaporation in vacuo, a solution of the residue in ethyl acetate was washed with water (3 times), saturated brine and dried (MgSO$_4$). The solvent was removed in vacuo and the residue purified by silica gel chromatography (eluting with 20–30% ethyl acetate in petroleum ether bp 60°–80° C.) to give the title compound as a crystalline solid. Found: C, 56.91; H, 4.21; N, 6.97. C$_{19}$H$_{15}$F$_6$N$_2$O requires: C, 56.72; H, 4.01; N, 6.96%.

EXAMPLE 11

L-1-((Bis(trifluoromethyl)phenyl)methyloxy)-2-N-formamido-2- phenylethane

L-2-Amino-1-((bis(trifluoromethyl)phenyl)methyloxy)-2-phenylethane (Description 2, free base, 1.2 g) was treated with formic acetic anhydride (prepared by heating acetic anhydride 0.5 g and formic acid 0.19 ml at 80° C. for 15 minutes) for 16 hours at room temperature. The solution was evaporated to dryness to give an oil which crystallized on standing. This solid was recrystallized from ethyl acetate/petroleum ether to give a mixture (approx 6:1) of L-1-((bis(trifluoromethyl)phenyl)methyloxy)-2-N-formamido-2-phenylethane and L-1-((bis(trifluoromethyl)phenyl)methyloxy)-2-N-acetamido-2-phenylethane mp 96°–99° C. Found: C, 55.50; H, 4.07; N, 3.49; C$_{18}$H$_{15}$NO$_2$F$_6$ requires C, 55.25; H, 3.86; N, 3.58%. m/e (Cl$^+$) 392 (M+H), (Cl$^-$)=390 (M–H).

The following examples illustrate pharmaceutical compositions according to the invention.

EXAMPLE 12A

Tablets Containing 1–25 mg of Compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 12B

Tablets Containing 26–100 mg of Compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 13

Parenteral Injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 1 ml |

The sodium phosphate, citric acid monohydrate and sodium chloride are dissolved in a portion of the water. The compound of formula (I) is dissolved or suspended in the solution and made up to volume.

EXAMPLE 14

Topical Formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1-receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 ug of the plasmid DNA into 10 million COS cells was achieved by electroporation in 800 µl of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM N-2-hydroxyethyl-piperazine-N'-2-ethane sulphonic acid (HEPES) pH 7.4) at 260 V and 950 µF using the IBI GENEZAPPER (trademark IBI, New Haven, Conn., USA). The cells were incubated in 10% fetal calf serum, 2 mM glutamine, 100 U/ml penicillin-streptomycin, and 90% DMEM media (GIBCO, Grand Island, N.Y., USA) in 5% $CO_2$ at 37° C. for three days before the binding assay.

B. Stable Expression in Chinese Hamster Ovarian Cell Line

To establish a stable cell line expressing cloned human NK1R, the cDNA was subcloned into the vector pRcCMV (INVITROGEN). Transfection of 20 ug of the plasmid DNA into CHO cells was achieved by electroporation in 800 µl of transfection buffer supplemented with 0.625 mg/ml Herring sperm DNA at 300 V and 950 µF using the IBI GENEZAPPER (IBI). The transfected cells were incubated in CHO media [10% fetal calf serum, 100 U/ml penicillin-streptomycin, 2 mM glutamine, 1/500 hypoxanthinethymidine (ATCC), 90% IMDM media (JRH BIOSCIENCES, Lenexa, Kans., USA), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}I$-substance P ($^{125}I$-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 µl of the cell suspension would give rise to about 10,000 cpm of specific $^{125}I$-SP binding (approximately 50,000 to 200,000 cells). In the binding assay, 200 ul of cells were added to a tube containing 20 ul of 1.5 to 2.5 nM of $^{125}I$-SP and 20 µl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholiphase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 5µCi of $^3H$-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3 nM to activate the human NK1R. After 30 min of incubation at 37° C., the medium is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The data in Table 1 were obtained for compounds of formula (I):

TABLE 1

| SUBSTANCE P ANTAGONISM RESULTS | |
|---|---|
| Compound of Ex # | $IC_{50}$ @ NK1R (nM) |
| 1 | 400 |
| 2 | 140 |
| 3 | 100 |
| 4 | 45 |
| 5 | 6 |
| 10 | 15 |
| 11 | 60 |

We claim:
1. A method for the treatment of pain, inflammation, migraine or postherpetic neuralgia, which method comprises administration to a patient in need thereof of a tachykinin-reducing amount of a compound of formula (I), or a pharmaceutically acceptable salt thereof:

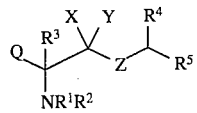

wherein

Q represents optionally substituted phenyl or optionally substituted naphthyl;

X and Y each represent H, $C_{1-6}$alkyl, $C_{2-6}$alkenyl or X and Y together form a group =O;

Z represents O or S;

$R^1$ represents H; $C_{1-6}$ alkyl optionally substituted by hydroxy, cyano, $COR^a$, $COOR^a$, $CONR^aR^b$, $COC_{1-4}alkylNR^aR^b$, $CONR^aC_{1-4}alkylCONR^aR^b$ or $NR^aR^b$, (where $R^a$ and $R^b$ each independently represent H, $C_{1-6}$ alkyl, phenyl optionally substituted by one or two of $C_{1-6}$alkyl, $C_{1-6}$alkoxy, halo or trifluoromethyl or phenyl($C_{1-4}$alkyl) optionally substituted in the phenyl ring by one or two of $C_{1-6}$ alkyl, $C_{1-6}$ alkoxy, halo or trifluoromethyl); phenyl($C_{1-4}$ alkyl) (optionally substituted in the phenyl ring by one or two of $C_{1-6}$ alkyl, $C_{1-6}$ alkoxy, halo or trifluoromethyl); $C_{2-6}$ alkenyl; $COR^a$; $COOR^a$; $CONHR^a$; $COC_{1-6}alkylhalo$; $COC_{1-6}alkylNR^aR^b$; or $CONR^aC_{1-6}alkylCONR^aR^b$, where $R^a$ and $R^b$ are as previously defined;

$R^2$ represents $C_{1-6}$ alkyl substituted by hydroxy, cyano, $COR^a$, $COOR^a$, $CONR^aR^b$, $COC_{1-4}alkylNR^aR^b$, $CONR^aC_{1-4}alkylCONR^aR^b$ or $NR^aR^b$, (where $R^a$ and $R^b$ are as above defined); phenyl($C_{1-4}$ alkyl) (optionally substituted by one or two of $C_{1-6}$ alkyl, $C_{1-6}$ alkoxy, halo and trifluoromethyl in the phenyl ring); $C_{2-6}$ alkenyl; $COR^a$; $COOR^a$; $CONHR^a$; $COC_{1-6}alkylhalo$; $COC_{1-6}alkylNR^aR^b$; or $CONR^aC_{1-6}alkylCONR^aR^b$, where $R^a$ and $R^b$ are as previously defined;

$R^3$ represents H or $C_{1-6}$alkyl;

$R^4$ represents H, $C_{1-6}$ alkyl or phenyl (optionally substituted by one or two of $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ each independently represent H, $C_{1-6}$ alkyl, phenyl or trifluoromethyl); and $R^5$ represents $(CH_2)_q$phenyl, wherein q is 0, 1, 2 or 3, which may optionally be substituted in the phenyl ring by one or two of $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined.

2. A method as claimed in claim 1 wherein $R^1$ represents H; $C_{1-6}$ alkyl optionally substituted by hydroxy, cyano, $COR^a$, $COOR^a$, $CONR^aR^b$, $COC_{1-4}alkylNR^aR^b$, $CONR^aC_{1-4}alkylCONR^aR^b$ or $NR^aR^b$, (where $R^a$ and $R^b$ each are as previously defined); phenyl($C_{1-4}$ alkyl) (optionally substituted in the phenyl ring by one or two of $C_{1-6}$ alkyl, $C_{1-6}$ alkoxy, halo and trifluoromethyl); $C_{2-6}$ alkenyl; $COR^a$; $COOR^a$; $CONHR^a$; $COC_{1-4}alkylNR^aR^b$; or $CONR^aC_{1-4}alkylCONR^aR^b$ (where $R^a$ and $R^b$ are as previously defined) and $R^2$ represents $C_{1-6}$ alkyl substituted by hydroxy, cyano, $COR^a$, $COOR^a$, $CONR^aR^b$, $COC_{1-4}alkylNR^aR^b$, $CONR^aC_{1-4}alkylCONR^aR^b$ or $NR^aR^b$, (where $R^a$ and $R^b$ each are as previously defined); phenyl($C_{1-4}$ alkyl) (optionally substituted in the phenyl ring by one or two of $C_{1-6}$ alkyl, $C_{1-6}$ alkoxy, halo and trifluoromethyl); $C_{2-6}$ alkenyl; $COR^a$; $COOR^a$; $CONHR^a$; $COC_{1-4}alkylNR^aR^b$; or $CONR^aC_{1-4}alkylCONR^aR^b$ (where $R^a$ and $R^b$ are as previously defined).

3. A method as claimed in claim 1 wherein $R^1$ represents H, $C_{1-6}$alkyl, phenyl($C_{1-4}$alkyl), $COR^a$, $COOR^a$ or $CONHR^a$, where $R^a$ is $C_{1-6}$ alkyl or phenyl, and $R^2$ represents phenyl($C_{1-4}$alkyl), $COR^a$, $COOR^a$ or $CONHR^a$, where $R^a$ is $C_{1-6}$ alkyl or phenyl.

4. A method as claimed in claim 1 wherein $R^1$ is H or methyl and $R^2$ is $C_{1-2}$alkyl substituted by a group selected from hydroxy, cyano, CHO, $CO_2(C_{1-6}alkyl)$, $CONR^aR^b$ and $NR^aR^b$.

5. A method as claimed in claim 1 wherein Q is unsubstituted or substituted phenyl; $R^4$ is H; and $R^5$ is substituted phenyl.

6. A method as claimed in claim 1 wherein X and Y both represent H and Z represents O.

7. A method as claimed in claim 1 wherein the compound of formula (I) is selected from:

L-1-((3,5-bis(trifluoromethyl)phenyl)methyloxy)-2-(t-butoxycarbonylamino)-2-phenylethane;

1-((3,5-dimethylphenyl)methyloxy)-2(S)-2-(((carbomethoxy) methyl)amino)-2-phenylethane;

(2S)-1-(((carboxamido)methyl)ammonium)-1-((3,5-dimethylphenyl)methyloxy)-2-phenylethane;

(2S)-1-((3,5-bis(trifluoromethyl)phenyl)methyloxy)-2-(((carbomethoxy)methyl)ammonium)-2-phenylethane;

(2S)-2-((3,5-bis(trifluoromethyl)phenyl)methyloxy)-2-(((carboxamido)methyl)ammonium)-2-phenylethane;

L-1-((3,5-bis(trifluoromethyl)phenyl)methyloxy)-2-((cyanomethyl)amino)-2-phenylethane;

L-1-((3,5-bis(trifluoromethyl)phenyl)methyloxy)-2-N-formamido-2-phenylethane;

or a pharmaceutically acceptable salt thereof.

8. A compound of formula (I'), or a pharmaceutically acceptable salt thereof:

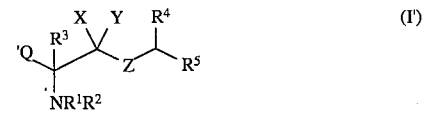

wherein

Q' represents unsubstituted or substituted phenyl;

X and Y each represent H, $C_{1-6}$alkyl, $C_{2-6}$alkenyl or X and Y together form a group =O;

Z represents O or S;

R¹ represents H; $C_{1-6}$ alkyl optionally substituted by hydroxy, cyano, $COR^a$, $COOR^a$, $CONR^aR^b$, $COC_{1-4}alkylNR^aR^b$, $CONR^aC_{1-4}alkylCONR^aR^b$ or $NR^aR^b$, (where $R^a$ and $R^b$ each independently represent H, $C_{1-6}$ alkyl, phenyl optionally substituted by one or two of $C_{1-6}$alkyl, $C_{1-6}$alkoxy, halo or trifluoromethyl or phenyl($C_{1-4}$alkyl) optionally substituted in the phenyl ring by one or two of $C_{1-6}$ alkyl, $C_{1-6}$ alkoxy, halo or trifluoromethyl); phenyl($C_{1-4}$ alkyl) (optionally substituted in the phenyl ring by one or two of $C_{1-6}$ alkyl, $C_{1-6}$ alkoxy, halo or trifluoromethyl); $C_{2-6}$ alkenyl; $COR^a$; $COOR^a$; $CONHR^a$; $COC_{1-6}$alkylhalo; $COC_{1-6}$alkylNR^aR^b$; or $CONR^aC_{1-6}alkylCONR^aR^b$, where $R^a$ and $R^b$ are as previously defined;

R² represents $C_{1-6}$ alkyl substituted by hydroxy, cyano, $COR^a$, $COOR^a$, $CONR^aR^b$, $COC_{1-4}alkylNR^aR^b$, $CONR^aC_{1-4}alkylCONR^aR^b$ or $NR^aR^b$, (where $R^a$ and $R^b$ are as above defined); phenyl($C_{1-4}$ alkyl) (optionally substituted by one or two of $C_{1-6}$ alkyl, $C_{1-6}$ alkoxy, halo and trifluoromethyl in the phenyl ring); $C_{2-6}$ alkenyl; $COR^a$; $COOR^a$; $CONHR^a$; $COC_{1-6}$alkylhalo; $COC_{1-6}alkylNR^aR^b$; or $CONR^aC_{1-6}alkylCONR^aR^b$, where $R^a$ and $R^b$ are as previously defined;

R³ represents H or $C_{1-6}$alkyl; and

R⁵ represents phenyl substituted by one or two groups selected from methoxy, nitro, cyano, halo and trifluoromethyl.

9. A compound selected from:

L-1-((3,5-bis(trifluoromethyl)phenyl)methyloxy)-2-(t-butoxycarbonylamino)-2-phenylethane;

1-((3,5-dimethylphenyl)methyloxy)-2(S)-2-(((carbomethoxy)methyl)amino)-2-phenylethane;

(2S)-1-(((carboxamido)methyl)ammonium)-1-((3,5-dimethylphenyl)methyloxy)-2-phenylethane;

(2S)-1-((3,5-bis(trifluoromethyl)phenyl)methyloxy)-2-(((carbomethoxy)methyl)ammonium)-2-phenylethane;

(2S)-2-((3,5-bis(trifluoromethyl)phenyl)methyloxy)-2-(((carboxamido)methyl)ammonium)-2-phenylethane;

L-1-((3,5-bis(trifluoromethyl)phenyl)methyloxy)-2-((cyanomethyl)amino)-2-phenylethane;

L-1-((3,5-bis(trifluoromethyl)phenyl)methyloxy)-2-N-formamido-2-phenylethane;

or a pharmaceutically acceptable salt thereof.

10. A pharmaceutical composition comprising a therapeutically effective amount of a compound as claimed in claim 8 in association with a pharmaceutically acceptable carrier.

11. A pharmaceutical composition comprising a therapeutically effective amount of a compound as claimed in claim 9 in association with a pharmaceutically acceptable carrier.

* * * * *